United States Patent [19]

Wiebe et al.

[11] Patent Number: 5,401,490
[45] Date of Patent: Mar. 28, 1995

[54] MARKERS OF TISSUE HYPOXIA

[75] Inventors: Leonard I. Wiebe; John R. Mercer; John D. Chapman; Rezaul H. Mannan; Vijayalakashmi Somayaji, all of Edmonton, Canada

[73] Assignee: Alberta Cancer Board, Edmonton, Canada

[21] Appl. No.: 978,873

[22] Filed: Nov. 19, 1992

Related U.S. Application Data

[63] Continuation of Ser. No. 492,810, Mar. 13, 1990, abandoned.

[30] Foreign Application Priority Data

Aug. 8, 1989 [CA] Canada .................................. 608739

[51] Int. Cl.⁶ .................. A61K 49/02; A61K 31/415; C12Q 1/68
[52] U.S. Cl. .................................. 424/1.73; 424/1.65; 424/1.81; 424/1.85; 424/9; 435/6; 514/25; 514/398
[58] Field of Search .................. 424/1.1, 9, 1.11, 1.65, 424/1.73, 1.81, 1.85; 435/6; 514/25, 43, 398; 536/23, 23.1

[56] References Cited

U.S. PATENT DOCUMENTS 4,462,992 7/1984 Agrawal et al. ...................... 514/43

OTHER PUBLICATIONS

Wiebe et al "Iodoazomycin Riboside [1-(5'-iodo-5'-deoxyribofuranosyl)-2-nitroimidazole], a Hypoxic Cell Marker In Vivo Evaluation in Experimental Tumors" in *Nuclear Medicine in Clinical Oncology* Ed. by C Winkler, Springer-Verlag (1986) pp. 402–407.

"Biochemistry of Reduction of Nitro Heterocycles"; John E. Biaglow, et al.; pp. 77–90.

"Contribution of Radionuclide Imaging to Radiation Oncology"; Carl M. Mansfield and Chan H. Park; *Seminars in Nuclear Medicine;* vol. XV, No. 1 (Jan, 1985); pp. 28–45.

"Radiosensitizers: Rationale and Potential"; J. Martin Brown; *Cancer Treatment Reports;* vol. 65 (Suppl. 2), 1981; pp. 95–102.

"Sucralose Overview"; *Splenda ® Brand Sweetner,* pp. 1–10.

*Primary Examiner*—Esther M. Kepplinger
*Assistant Examiner*—Lora M. Green
*Attorney, Agent, or Firm*—Bell, Seltzer, Park & Gibson

[57] ABSTRACT

Novel nucleosides are provided having at least one hydrogen or hydroxide substitutent replaced by a γ-emitting halogen. Methods of preparation of these nucleosides are provided and also a novel non-invasive method for the detection and measurement of tissue hypoxia in mammals.

5 Claims, 7 Drawing Sheets

MARKERS OF TISSUE HYPOXIA

This application is a continuation of application Ser. No. 07/492,810, filed Mar. 13, 1990, abandoned.

This invention relates to sugar coupled 2-nitroimidazoles which demonstrate hypoxic cell selectivity. More particularly, this invention relates to novel azomycin nucleosides which are useful as probes for assessing tissue oxygenation status non-invasively, to methods for preparing these nucleosides and to non-invasive techniques for assessing tissue oxygenation status.

Hypoxic cells are known to exist in both animal (1) (see list of references infra) and human (2) tumor lines and this cell population has been shown to be 2.5 to 3× more resistant than normally oxygenated cells to therapeutic radiation (3). The presence of these radioresistant populations in tumors presents a serious obstacle to the curative potential of clinical radiotherapy. The surviving viable hypoxic cells may lead to regrowth of the tumor necessitating further treatment. The presence of hypoxic tissues in tumors has a profound influence on their ultimate curability by radiotherapy. An accurate assessment of the presence and extent of hypoxic tissues in tumors would be of invaluable assistance in designing a therapeutic regimen and in following the response of tumor tissue to therapy. A variety of methods has been proposed for the detection and measurement of hypoxic cells in tumors (4). To date there is no practical, clinically useful method. Many experimental techniques to assess tumor hypoxia are invasive or impractical in a clinical setting.

one promising approach to the assessment of hypoxic tissue is suggested by the ability of certain classes of compounds to selectively localize in these tissues after intravenous administration. The radiosensitizing drug, misonidazole (MISO), was shown to become selectively bound to the macromolecular fraction of EMT-6 murine tumor and V-79 hamster cells in hypoxic in vitro incubation studies (5) and to EMT-6 tumors in BALB/C mice (6) in an in vivo study. Selective binding of a γ-emitting analogue of a suitable compound would allow imaging and measurement of hypoxic tissue by conventional nuclear medicine techniques. Based on this approach, a number of analogues of 2-nitroimidazole heterocycles have been investigated as potential non-invasive, hypoxic tissue specific, nuclear medicine imaging agents. The selective toxicity to hypoxic cells by 2-nitroimidazole has been shown to correlate with the accumulation of cellular reduction products of these compounds (4) .

The exact mechanism of the binding to the macromolecular fraction of cells remains under investigation, but relies on reduction of the nitroheterocycle through a series of one-electron transfers to nitroso, hydroxylamino and amino products (7). This process is reliant on flavoproteins known as nitroreductases. The mediation of enzymes requires that the cells are viable and the progression of the reduction past the one-electron adduct (nitro radical anion) requires that oxygen is not present since this species inhibits the progress of the reduction by accepting the electron from the nitro radical anion thereby regenerating the nitroheterocycle. The reductive metabolism and subsequent binding will therefore only be expected to take place in poorly oxygenated yet viable (hence hypoxic) cells.

A number of experimental hypoxic tissue imaging agents incorporating γ-emitting radionuclides have been investigated. These include 4-bromomisonidazole (8, 9), 1-(2-(2-iodophenoxy)-ethyl)-2-nitroimidazole (10), a series of iodinated acetophenone derivatives of 2-nitroimidazole (11), fluoromisonidazole (12) and the 2-nitroimidazole nucleoside analogue, iodoazomycin riboside (IAZR) (13, 14). This latter compound demonstrated greater hypoxic cell toxicity and rates of binding than MISO in in vitro testing (13) but was subject to metabolic deiodination when in vivo studies were performed (14) and was therefore not useful for clinical purposes.

According to one aspect, the present invention provides novel nucleosides having the general formula

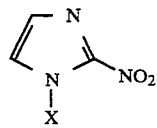

wherein X is a monosaccharide having 5 or 6 carbon atoms, other than ribose, said monosaccharide having at least one hydrogen or hydroxide substituent replaced by a γ-emitting halogen.

D and L forms and α and β anomers of the compounds of the above general formula are included within the present invention.

The term "γ-emitting halogens", as used herein, includes both direct and co-incident γ-emitting halogen isotopes. Direct γ-emitting halogen isotopes include $^{123}I$, $^{125}I$ and $^{131}I$ and co-incident γ-emitting isotopes include $^{124}I$ and $^{18}F$.

According to a further aspect of the invention, a process is disclosed for preparation of novel nucleosides having the general formula

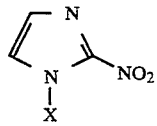

wherein X is a monosaccharide having 5 or 6 carbon atoms, other than ribose, said monosaccharide having at least one hydrogen or hydroxide substituent replaced by a γ-emitting halogen, said process comprising the following steps:

(a) coupling a monosaccharide having 5 or 6 carbon atoms, other than ribose, with 2-nitroimidazole; and (b) replacing at least one hydrogen or hydroxyl substituent of said monosaccharide with a γ-emitting halogen atom; or (c) replacing at least one hydrogen or hydroxyl substituent of said monosaccharide with a halogen atom followed by exchanging said halogen atom with a γ-emitting halogen atom. According to a further aspect of the invention, a novel non-invasive method is provided for the detection and measurement of tissue hypoxia in a mammal comprising the steps of (a) administering to the mammal a nucleoside having the general formula

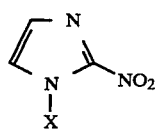

wherein X is a monosaccharide having 5 or 6 carbon atoms, other than ribose, said monosaccharide having at least one hydrogen or hydroxide substituent replaced by a suitable γ-emitting halogen;

(b) allowing said nucleoside to be taken up selectively by the hypoxic tissue; and (c) detecting and quantitating the γ-emission from said halogen.

Azomycin (2-nitroimadazole) analogues are reduced within mammalian cells to activated species which covalently bind to cellular molecules. The rate of drug binding is inversely proportional to intracellular oxygen concentration and closely mimics the oxygen dependency of radiation-induced cell killing. The selective hypoxia-dependent binding of γ-emitting nitroimidazoles makes them potential diagnostic agents for the in vivo scintigraphic detection and assessment of tissue hypoxia. We have proposed that such drug adducts might be labelled with an appropriate γ-emitting radioisotope for the purpose of detecting tissue oxygenation status non-invasively by techniques of conventional nuclear medicine.

Novel halogenated azomycin nucleosides have been synthesised and tested in animal tumor models for their ability to define tissue hypoxia by non-invasive procedures.

Preferred embodiments of the present invention, which show exquisite hypoxic tissue-marking ability, are the compounds 1-(5-deoxy-5-iodo-β-D-arabinofuranosyl)-2-nitroimidazole (iodoazomycin arabinoside or IAZA); 1-(6-deoxy-6-iodo-β-D-galactopyranosyl)-2-nitroimidazole (iodoazomycin galactoside or IAZG); and 1-(4-deoxy-4-iodo-β-L-xylopyranosyl)-2-nitroimidazole (iodoazomycin pyranoside or IAZP), labelled with a suitable γ-emitting iodine isotope.

Their bio-distribution and high tissue uptake levels combined with their in vivo stability make them useful probes for measuring tissue oxygenation status non-invasively by nuclear medicine techniques, by both planar and tomographic imaging techniques.

It is known to those skilled in the art that the compounds of the invention may be labelled with any γ-emitting halogen suitable for scintigraphic detection in humans, including $^{123}I$, $^{124}I$, $^{131}I$ and $^{18}F$ and that compounds labelled with $^{125}I$ are suitable for in vitro testing and small animal studies.

Since radiation resistance and some chemotherapeutic drug resistance correlate with tumor hypoxia, the ability to define one type of tumor resistance in advance of therapy is important, since several new modalities of cancer treatment are directed towards treatment-resistant hypoxic cells.

In addition, a nuclear medicine probe for oxygenation status will be useful also in detecting and defining other disease states, including myocardial infarct and cerebrovascular hemorrhage, in which ischemia and/or infarct play a role and in infections which involve anaerobic foci.

The invention, as exemplified by preferred embodiments, is described with reference to the drawings in which.

Both IAZA and IAZG are synthesised, in high yield, from commercial precursors (FIG. 1) and undergo high-yield isotope exchange reactions with radioiodine to produce the required radiolabelled test compounds. Long term storage in solution results in some decomposition of the pure compounds, presumably due to cleavage of the sugar from the heterocycle. Therefore, the compounds were stored as a dry residue in multidose vials under refrigeration and were reconstituted with the appropriate solvent just prior to use. IAZP is similarly synthesised. It will be known to those skilled in the art that other radio halogens may be similarly employed in the exchange reaction.

Both IAZG and IAZA show selective toxicity to hypoxic EMT-6 tumor cells and also sensitise these cells to the lethal effects of ionising radiation. IAZA is taken up preferentially in EMT-6 tumor tissue at a level useful for non-invasive imaging. An imaging study using $^{125}I$-IAZA showed EMT-6 tumor tissue to be clearly delineated from surrounding tissue.

Figure 10:
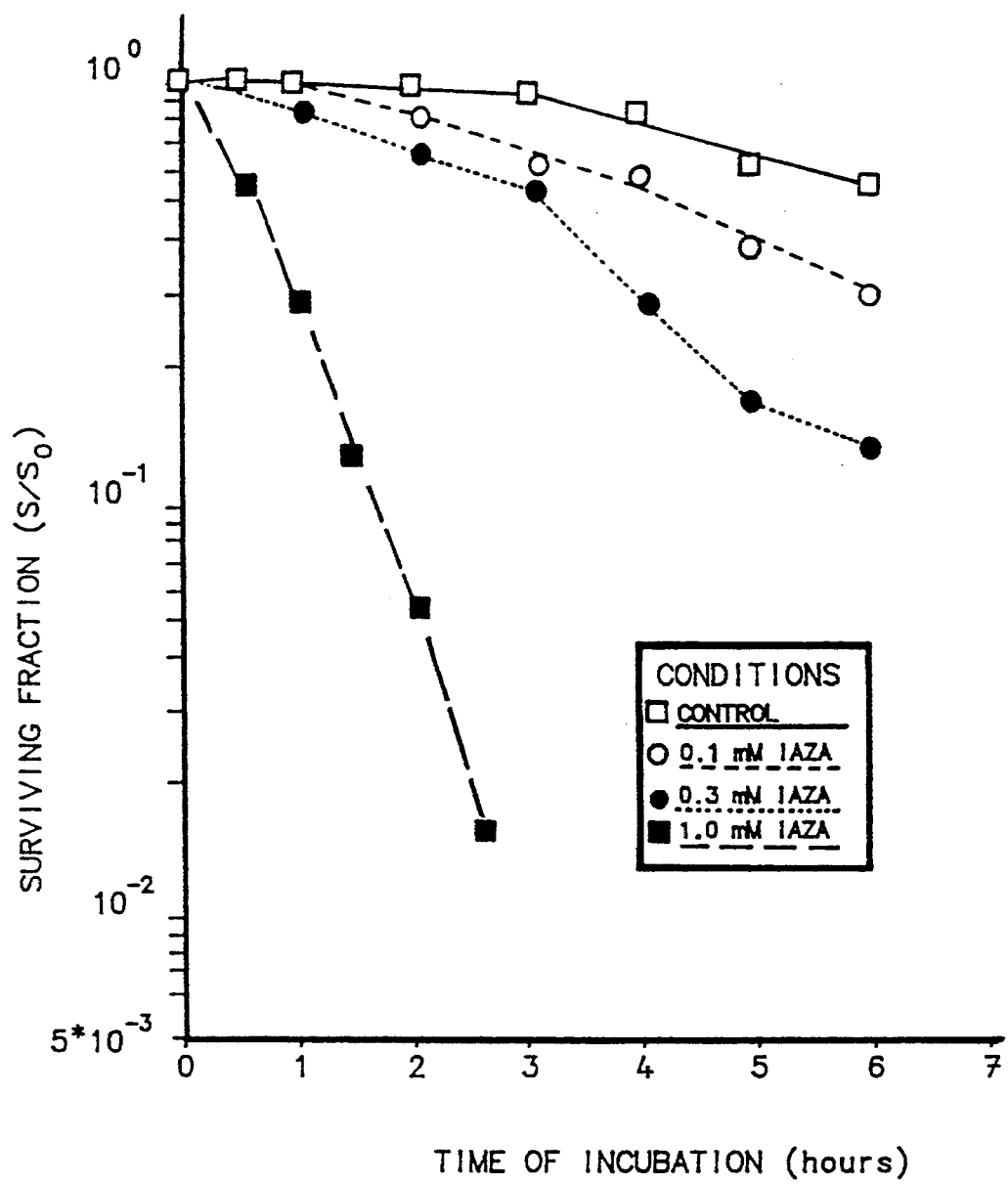
FIG. 10 shows surviving fractions of EMT-6 cells incubated with various concentrations of IAZA.

FIG. 10 shows the surviving fraction of EMT-6 cells in culture after exposure to various concentrations of IAZA under hypoxic incubation conditions at 37° C.

Figure 2:
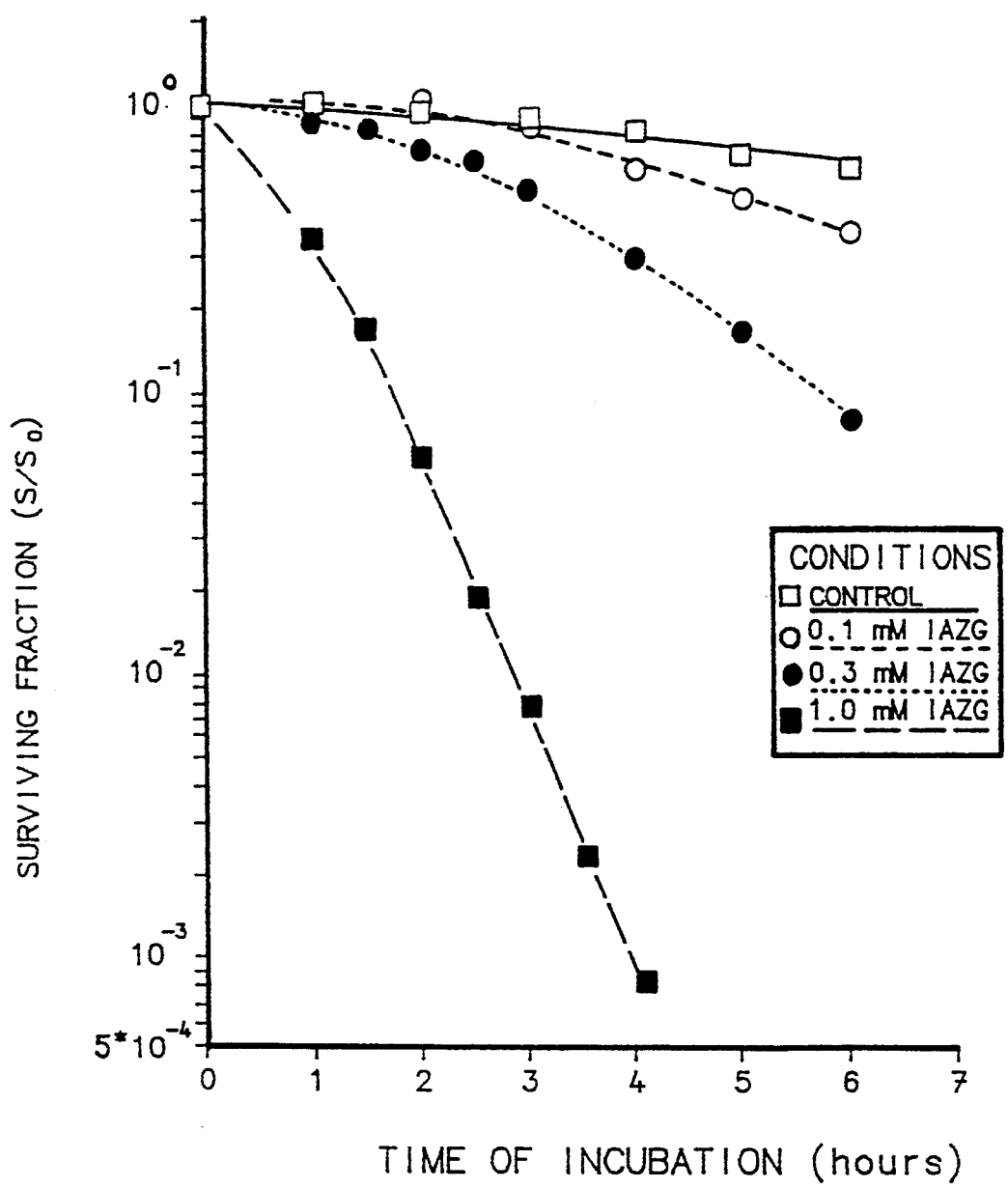
FIG. 2 shows surviving fractions of EMT-6 cells after incubation with various concentrations of IAZG.

FIG. 2 shows the surviving fraction of EMT-6 cells in culture after exposure to various concentrations of IAZG under hypoxic incubation conditions at 37° C. The increasing cytotoxity with drug concentration and the absence of toxicity under oxic conditions is characteristic of hypoxic radiosensitizers and other bio reductive alkylating drugs. The time required to reduce the cell population by 90% at 1.0 mM IAZG is about 1.75 h, approximately equivalent to IAZA (1.65 h). This represents a cytosidal toxicity about 10× that of MISO under the same conditions.

Figure 3B:
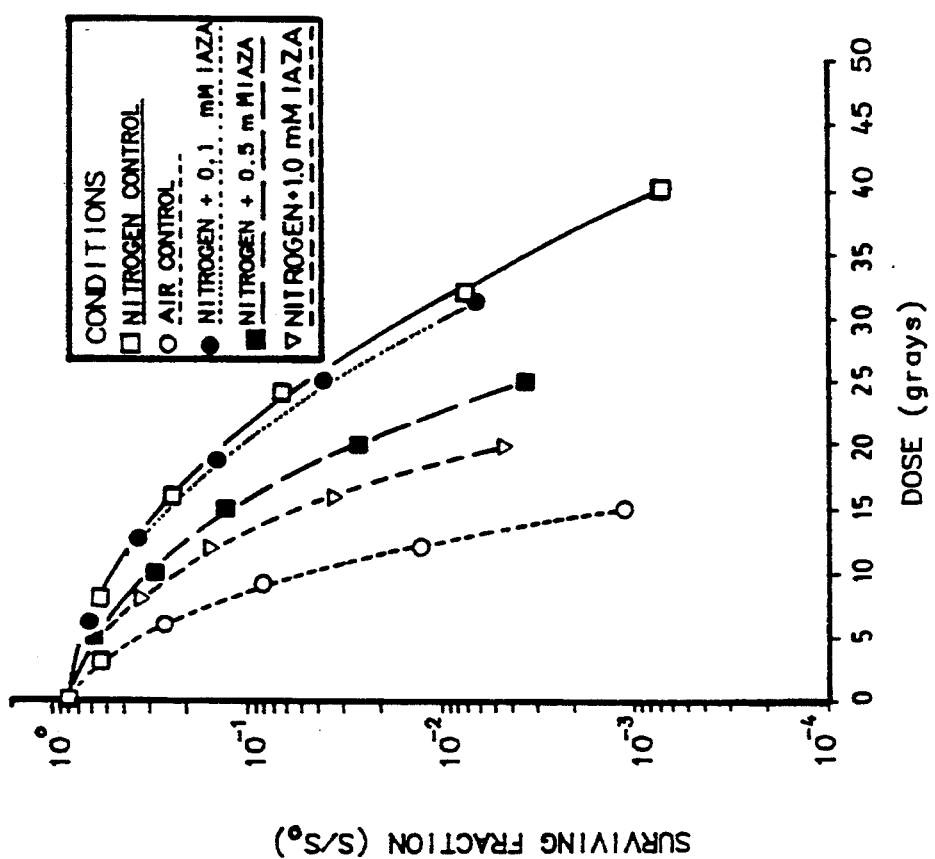
FIG. 3A and 3B show surviving fractions of EMT-6 cells irradiated with various doses of $^{137}Cs$ γ-rays in air, nitrogen and nitrogen plus various concentrations of IAZG (left curves) and IAZA (right curves).
Figure 3A:
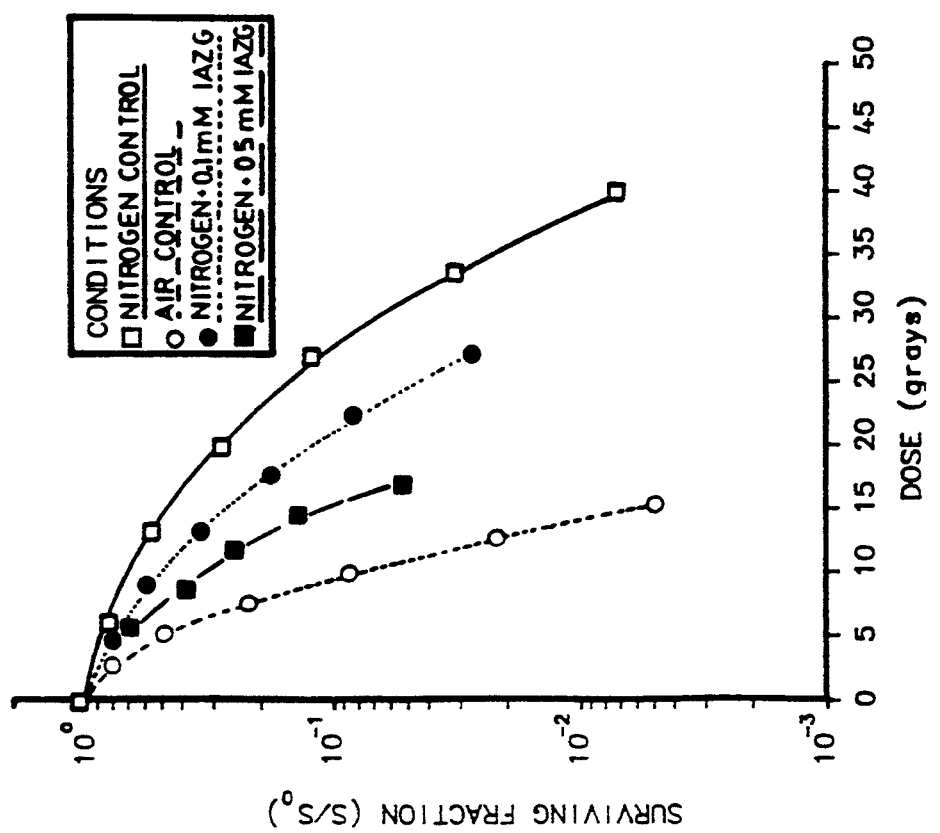

FIG. 3A and 3B show the radiation sensitivity of EMT-6 cells in vitro under hypoxic and aerobic conditions and in the presence of various concentrations of IAZG and IAZA. These figures show the enhancement of radiation sensitivity as previously observed for other electron-affinic radiosensitizers such as MISO and IAZR (13). The sensitizer enhancement ratio (SER) (calculated as the radiation dose required for a 90% cell kill under hypoxic incubation without and with test drug) is qualitatively similar for the two compounds IAZG and IAZA with the ratios being somewhat higher for IAZG. At 50 μM concentration the SER for IAZG and IAZA, at about 1.8 and 1.4 respectively, are comparable with the previously determined riboside IAZR (1.6) and somewhat greater than MISO (1.2). IAZG is the most efficient in vitro radiosensitizer of the azomycin nucleoside class produced to date.

Figure 4:
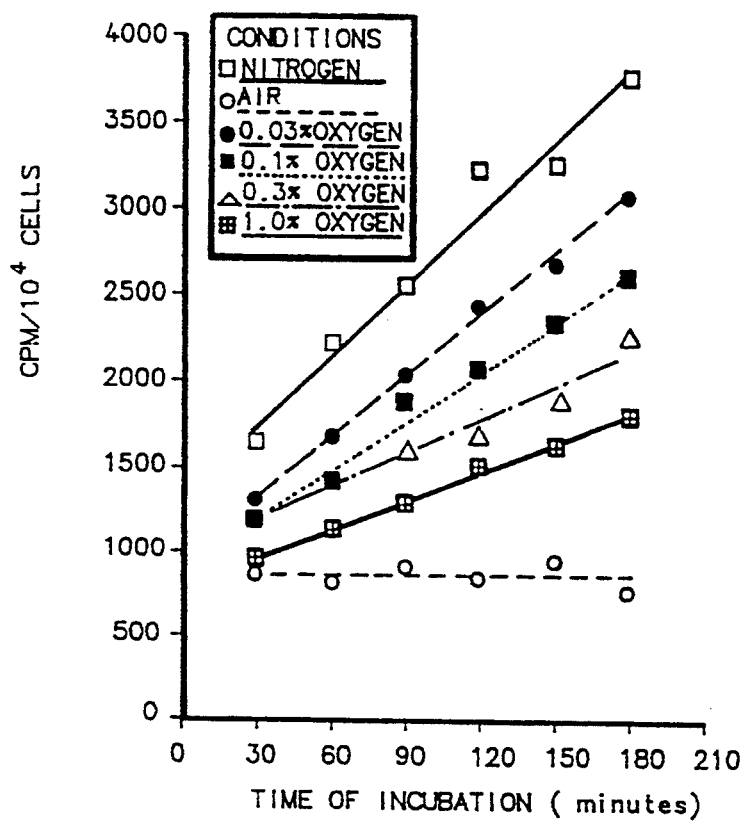
FIG. 4 shows the amount of radioactivity bound to the acid insoluble fraction of EMT-6 cells in vitro after incubation with 10 μM IAZG under aerobic and hypoxic conditions and at several intermediate levels of oxygenation.

The binding of IAZG to the acid precipitable fraction of EMT-6 cells in vitro is dependent on the degree of hypoxia as shown in FIG. 4. This oxygen dependent binding study shows that the greatest uptake of IAZG occurs under nitrogen incubation with a decrease in the binding rate as the oxygen concentration to which the cells are exposed is increased. The binding appears to increase linearly with time. To assess the relative efficiency of uptake of the test compounds, the initial binding rate in terms of pmol/$10^6$ cells/h was determined at several different concentrations. These data are presented in FIG. 5 and demonstrate that IAZG has a higher binding rate than IAZA or MISO. This is the highest binding rate measured to date for any 2-nitroimidazole derivative and is 4 to 8 times greater than MISO.

Figure 8:
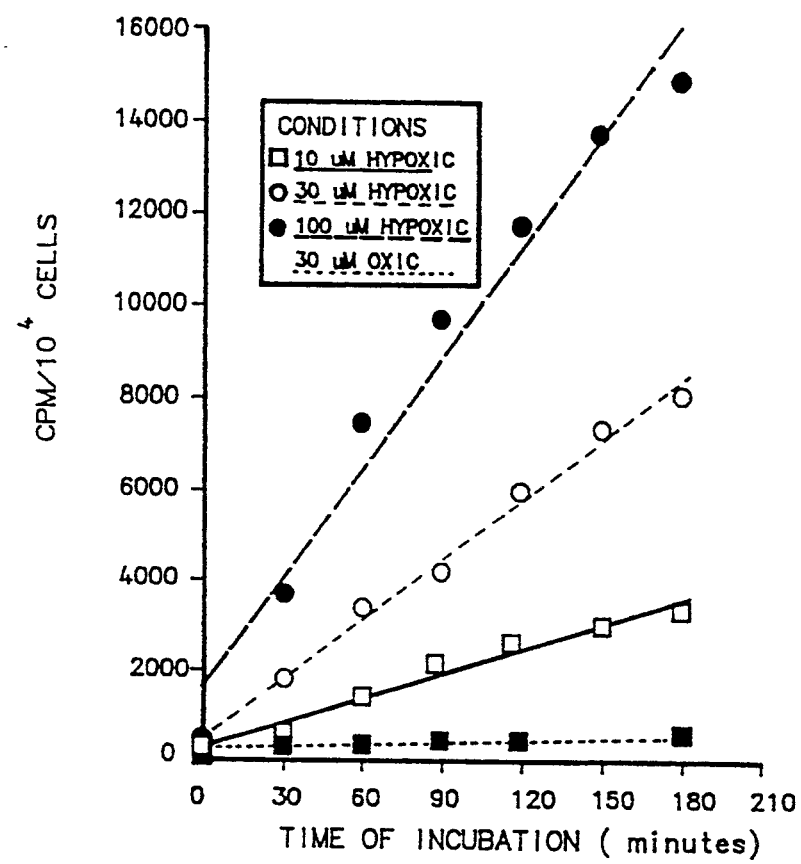
FIG. 8 shows uptake of radioactivity into the acid insoluble fraction of EMT-6 cells during incubation with various concentrations of $^{125}I$-IAZA under oxic and hypoxic conditions at 37° C.
Figure 9:
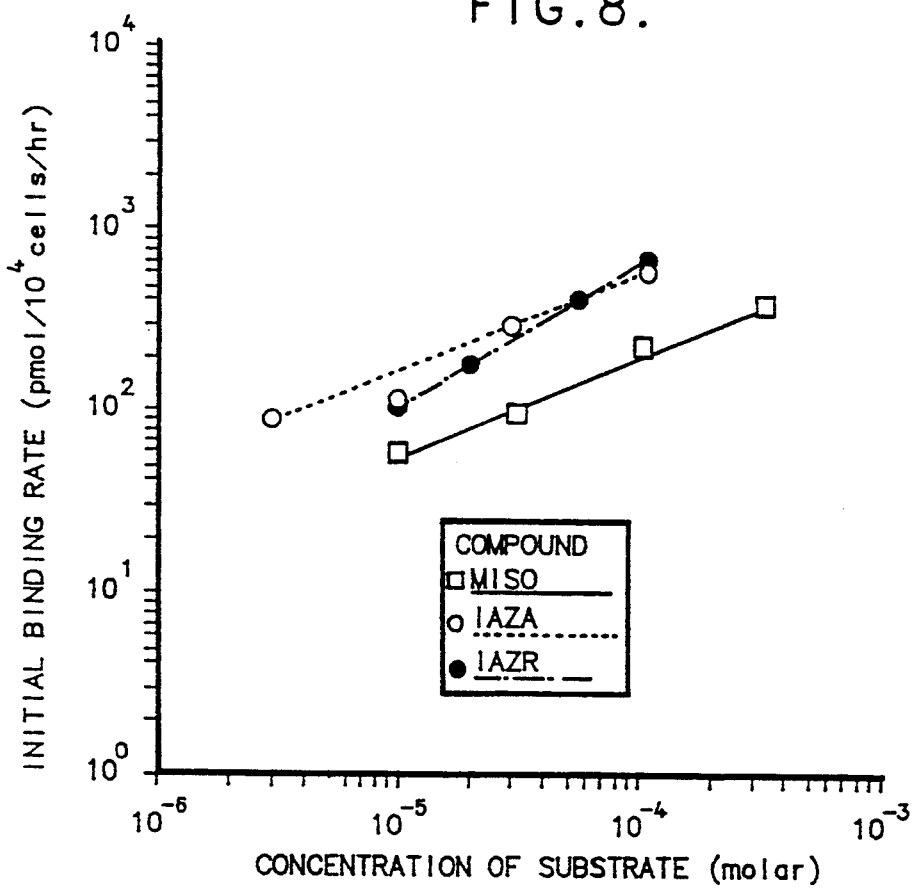
FIG. 9 shows initial binding rate of $^{125}I$-IAZA to the acid insoluble fraction of EMT-6 cells under hypoxic conditions at 37° C.

The binding of IAZA to the acid precipitable fraction of EMT-6 cells in vitro is shown in FIG. 8 and the initial binding rate of IAZA to the acid insoluble fraction under hypoxic conditions at 37° C. is in FIG. 9.

Figure 6:
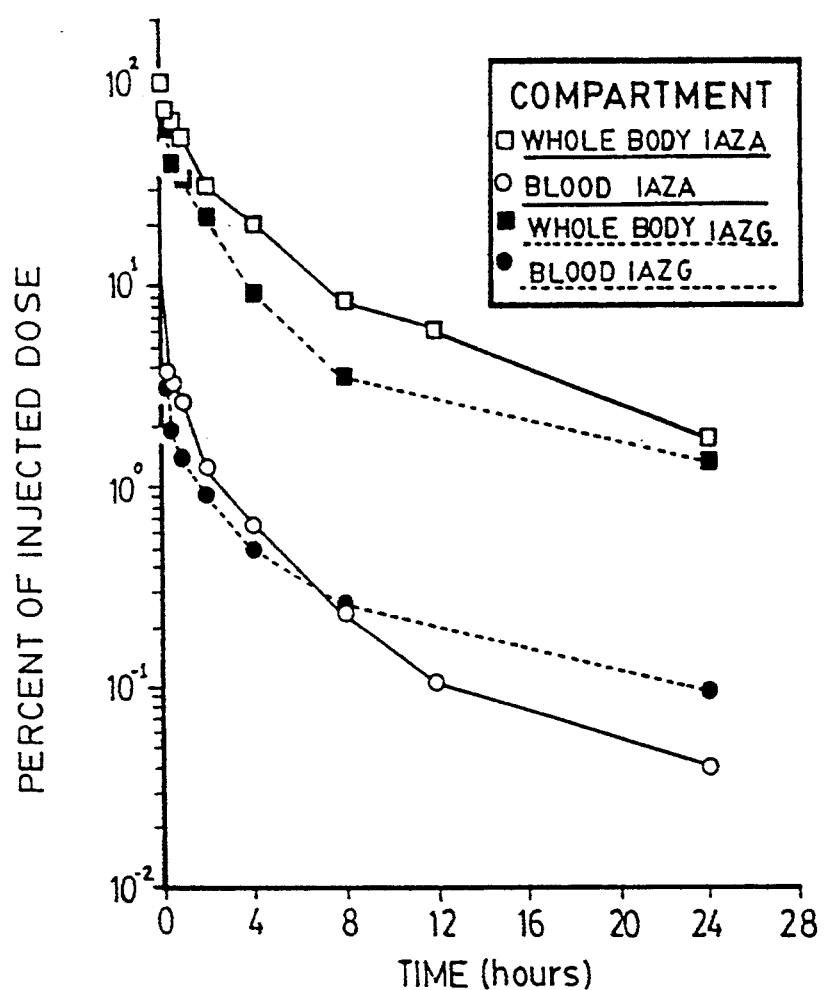
FIG. 6 shows blood clearance and whole body elimination of radioactivity from BALB/C mice bearing subcutaneous EMT-6 tumors after intravenous injection of $^{125}I$-IAZG and $^{125}I$-IAZA. Each data point represents the mean of 6 animals.

In vivo tissue distribution of IAZG and IAZA in BALB/C mice bearing EMT-6 tumors is shown in Tables 1 and 2 respectively. Tables 1 and 2 show the percent of injected IAZG and IAZA respectively per gram of wet tissue for selected tissues excised from BALB/C mice bearing EMT-6 tumors. This tumor model is known to have a high hypoxic fraction (0.33) (16). FIG. 6 shows the percent of injected dose in the whole body and in the blood at various time intervals after intravenous bolus administration of $^{125}$I-labelled IAZG and IAZA. These data demonstrate that both compounds undergo initial rapid blood clearance and rapid excretion of radioactivity from the body. In both cases the initial clearance rates are greater for IAZG than IAZA. The major route of excretion is via the urine as demonstrated by the high radioactivity in the kidney at short time periods. Hepatobiliary excretion may play a role in blood clearance as evidenced by elevated liver radioactivity and the appearance of activity in the intestine. Some oxidative or reductive metabolites of the 2-nitroimidazoles may also become bound to liver tissue, as was postulated in an in vivo study with $^{14}$C-MISO (6). This supposition is supported by the persistence of liver radioactivity at longer time periods. Both compounds show evidence of deiodination at longer periods (>4 h) as indicated by the increase in thyroid radioactivity. At 8 and 24 hours thyroid levels of IAZG are 7.2 and 30.9% of the total body activity and for IAZA they are 7.9 and 33.8% of total body activity.

TABLE 1

Percent of Injected Dose per Gram of Tissue of BALB/C Mice Bearing Subcutaneous EMT-6 Tumors after Intravenous Injection of $^{125}$I-IAZG. The Data are the Mean Values for n = 6, ± Standard deviation. The Values in Parentheses are Tissue to Blood Ratios.

| Organ | Time (hours) | | | | | | |
|---|---|---|---|---|---|---|---|
| | 0.25 | 0.50 | 1 | 2 | 4 | 8 | 24 |
| Blood | 1.83 ± 0.17 | 1.11 ± 0.16 | 0.86 ± 0.26 | 0.53 ± 0.10 | 0.28 ± 0.07 | 0.16 ± 0.03 | 0.06 ± 0.02 |
| Tumor | 1.75 ± 0.46 | 1.45 ± 0.24 | 1.21 ± 0.21 | 0.77 ± 0.17 | 0.43 ± 0.09 | 0.23 ± 0.09 | 0.08 ± 0.01 |
| | (0.95) | (1.31) | (1.47) | (1.45) | (1.56) | (1.34) | (1.41) |
| Kidney | 15.64 ± 1.15 | 8.94 ± 1.20 | 4.56 ± 1.41 | 2.67 ± 0.51 | 1.10 ± 0.29 | 0.40 ± 0.02 | 0.09 ± 0.03 |
| | (8.58) | (8.07) | (5.56) | (5.06) | (4.00) | (2.47) | (1.52) |
| Liver | 5.50 ± 0.79 | 2.96 ± 0.49 | 1.48 ± 0.24 | 1.40 ± 0.56 | 0.43 ± 0.12 | 0.20 ± 0.02 | 0.08 ± 0.02 |
| | (3.00) | (2.66) | (1.82) | (2.55) | (1.51) | (1.24) | (1.32) |
| Muscle | 1.31 ± 0.21 | 0.70 ± 0.18 | 0.37 ± 0.19 | 0.34 ± 0.20 | 0.14 ± 0.03 | 0.06 ± 0.02 | 0.02 ± 0.01 |
| | (0.72) | (0.63) | (0.48) | (0.62) | (0.49) | (0.36) | (0.38) |
| Intestine | 6.82 ± 5.20 | 3.65 ± 1.36 | 1.16 ± 0.25 | 0.82 ± 0.45 | 0.29 ± 0.07 | 0.17 ± 0.08 | 0.05 ± 0.02 |
| | (3.65) | (3.19) | (1.42) | (1.48) | (1.04) | (1.05) | (0.83) |
| Stomach | 3.29 ± 1.07 | 2.14 ± 1.01 | 1.38 ± 0.42 | 1.49 ± 1.12 | 0.55 ± 0.30 | 0.42 ± 0.35 | 0.06 ± 0.04 |
| | (1.79) | (1.92) | (1.64) | (2.61) | (1.85) | (2.50) | (0.87) |
| Lung | 2.77 ± 0.44 | 1.46 ± 0.24 | 0.74 ± 0.12 | 0.61 ± 0.17 | 0.33 ± 0.09 | 0.16 ± 0.02 | 0.07 ± 0.01 |
| | (1.51) | (1.31) | (0.90) | (1.13) | (1.16) | (0.98) | (1.26) |

TABLE 2

Percent of Injected Dose Per Gram of Tissue in BALB/C Mice Bearing Subcutaneous EMT-6 Tumors after Intravenous Injection of $^{125}$I-IAZA. The Data are the Mean Values for n = 6, ± Standard Deviation. The Values in Parentheses are Tissue to Blood Ratios.

| Organ | Time (hours) | | | | | | |
|---|---|---|---|---|---|---|---|
| | 0.25 | 0.50 | 1 | 2 | 4 | 8 | 24 |
| Blood | 2.63 ± 0.28 | 2.17 ± 0.85 | 1.84 ± 0.72 | 0.91 ± 1.56 | 0.45 ± 1.24 | 0.14 ± 0.07 | 0.037 ± 0.047 |
| Tumor | 2.55 ± .86 | 3.48 ± .46 | 2.70 ± .39 | 2.55 ± 1.65 | 2.08 ± .27 | 1.22 ± .24 | 0.206 ± .23 |
| | (0.97) | (1.60) | (1.46) | (2.80) | (4.62) | (8.71) | (5.56) |
| Kidney | 6.56 ± 0.63 | 5.67 ± 0.95 | 4.38 ± 1.25 | 1.80 ± 0.61 | 0.66 ± 0.39 | 0.34 ± 0.06 | 0.52 ± 0.004 |
| | (2.49) | (2.61) | (2.38) | (1.98) | (1.46) | (2.43) | (1.41) |
| Liver | 8.65 ± 1.02 | 7.14 ± 1.13 | 5.63 ± 2.27 | 2.18 ± 0.80 | 0.95 ± 0.58 | 0.47 ± 0.10 | 0.098 ± 0.008 |
| | (3.29) | (3.29) | (3.06) | (2.39) | (2.11) | (3.36) | (2.64) |

TABLE 2-continued

Percent of Injected Dose Per Gram of Tissue in BALB/C Mice Bearing Subcutaneous EMT-6 Tumors after Intravenous Injection of $^{125}$I-IAZA. The Data are the Mean Values for n = 6, ± Standard Deviation. The Values in Parentheses are Tissue to Blood Ratios.

| Organ | \multicolumn{7}{c}{Time (hours)} | | | | | | |
|---|---|---|---|---|---|---|---|
| | 0.25 | 0.50 | 1 | 2 | 4 | 8 | 24 |
| Heart | 4.69 ± 0.91 (1.78) | 3.56 ± 0.66 (1.64) | 2.78 ± 1.30 (1.51) | 1.03 ± 0.43 (1.13) | 0.32 ± 0.24 (0.71) | 0.22 ± 0.05 (1.57) | 0.042 ± 0.017 (1.14) |
| Spleen | 3.57 ± 0.67 (1.36) | 3.00 ± 0.62 (1.38) | 2.48 ± 1.25 (1.35) | 0.93 ± 0.37 (1.02) | 0.35 ± 0.20 (0.78) | 0.18 ± 0.04 (1.29) | 0.036 ± 0.034 (0.97) |
| Muscle | 3.09 ± 0.67 (1.17) | 2.77 ± 0.54 (1.28) | 2.19 ± 1.03 (1.19) | 0.69 ± 0.29 (0.75) | 0.24 ± 0.12 (0.53) | 0.36 ± 0.31 (2.57) | 0.020 ± 0.004 (0.54) |
| Bone | 1.31 ± 0.18 (0.50) | 1.37 ± 0.57 (0.63) | 1.15 ± 0.52 (0.63) | 0.58 ± 0.26 (0.64) | 0.27 ± 0.09 (0.60) | 0.08 ± 0.03 (0.57) | 0.022 ± 0.03 (0.59) |
| Intestine | 5.42 ± 1.03 (2.06) | 4.44 ± 0.62 (2.04) | 4.63 ± 1.92 (2.52) | 1.73 ± 0.55 (1.90) | 0.81 ± 0.46 (1.80) | 0.77 ± 0.36 (5.50) | 0.041 ± 0.016 (1.11) |
| Stomach | 4.36 ± 0.70 (1.66) | 4.75 ± 1.05 (2.19) | 3.95 ± 0.93 (2.15) | 3.30 ± 0.93 (3.62) | 1.81 ± 1.60 (4.02) | 0.87 ± 0.54 (6.21) | 0.067 ± 0.014 (1.81) |
| Lung | 4.61 ± 0.82 (1.75) | 3.77 ± 0.67 (1.74) | 2.99 ± 1.41 (1.63) | 1.15 ± 0.38 (1.26) | 0.45 ± 0.30 (1.00) | 0.33 ± 0.07 (2.36) | 0.037 ± 0.008 (1.00) |
| Carcass | 2.68 ± 0.44 (1.02) | 2.55 ± 0.37 (1.18) | 2.23 ± 0.91 (1.21) | 1.46 ± 0.29 (1.60) | 0.89 ± 0.52 (1.98) | 0.28 ± 0.12 (2.00) | 0.038 ± 0.016 (1.03) |

Figure 7:
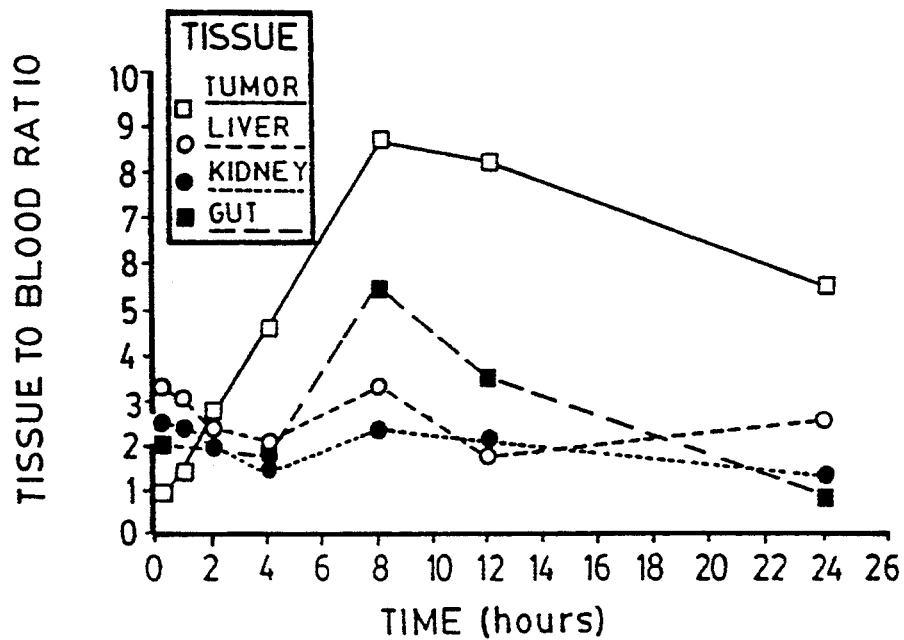
FIG. 7 shows tissue to blood ratio of radioactivity levels for selected tissues in BALB/C mice bearing subcutaneous EMT-6 tumors after intravenous injection of $^{125}I$-IAZA.

IAZG and IAZA differ markedly in their uptake into EMT-6 tumor tissue. IAZG shows a maximal tumor to blood ratio of 1.56 at 4 h representing 0.23% of the injected dose and IAZA has a maximum tumor to blood ratio of 8.7 at 8 h representing 1.22% of the injected dose. At 24 h, tumor to blood ratio of IAZA is still in excess of 5.5 (FIG. 7). The physical or biochemical process leading to the qualitative difference in tumor uptake for the two compounds has not been determined. It is possible that IAZA undergoes facilitated transport into EMT-6 tumor cells in vivo via non-specific nucleoside transporters. The actual uptake of IAZG into hypoxic tumor tissue in vivo may in fact be better than indicated by Table 1 since these data are taken from total excised tumor which includes both oxic and hypoxic cells and often necrotic tissue. If the activity in these tumors resides mainly in the hypoxic fraction, the tumor to blood ratios for this subpopulation of cells would be in the order of three times greater than the values reported in Table 1.

The following examples are illustrative only and not intended as limiting with respect to the present invention.

EXAMPLE 1

Chemicals and solvents were of reagent grade. Solvents were purified by distillation and were dried by standard techniques. Uncorrected melting points were determined by a Büchi melting point apparatus. $^1$H and $^{13}$C NMR spectra were recorded on a Brucker AM-300 spectrometer using tetramethylsilane as internal reference. High resolution mass spectrometry (HRMS) was determined on an AEI MS 50 mass spectrometer and was used to determine the elemental composition. High pressure liquid chromatography (HPLC) analyses were carried out in a Waters system with an ultraviolet detector set at a wavelength of 350 nm. Radioactive column effluent was monitored by a NaI(Tl) scintillation detector. Analytical and small scale preparative HPLC separations were performed using a Waters C-18 Radial-Pake reverse phase column. Thin-layer chromatography plates from Whatman (MK6F-microslides) were used throughout. Radioiodine was purchased from the Edmonton Radiopharmaceutical Center ($^{125}$I, $^{131}$I) or Nordion International Inc., Vancouver ($^{123}$I). Tissue samples were counted in a Beckman Gamma 8000 gamma scintillation counter.

Figure 1:
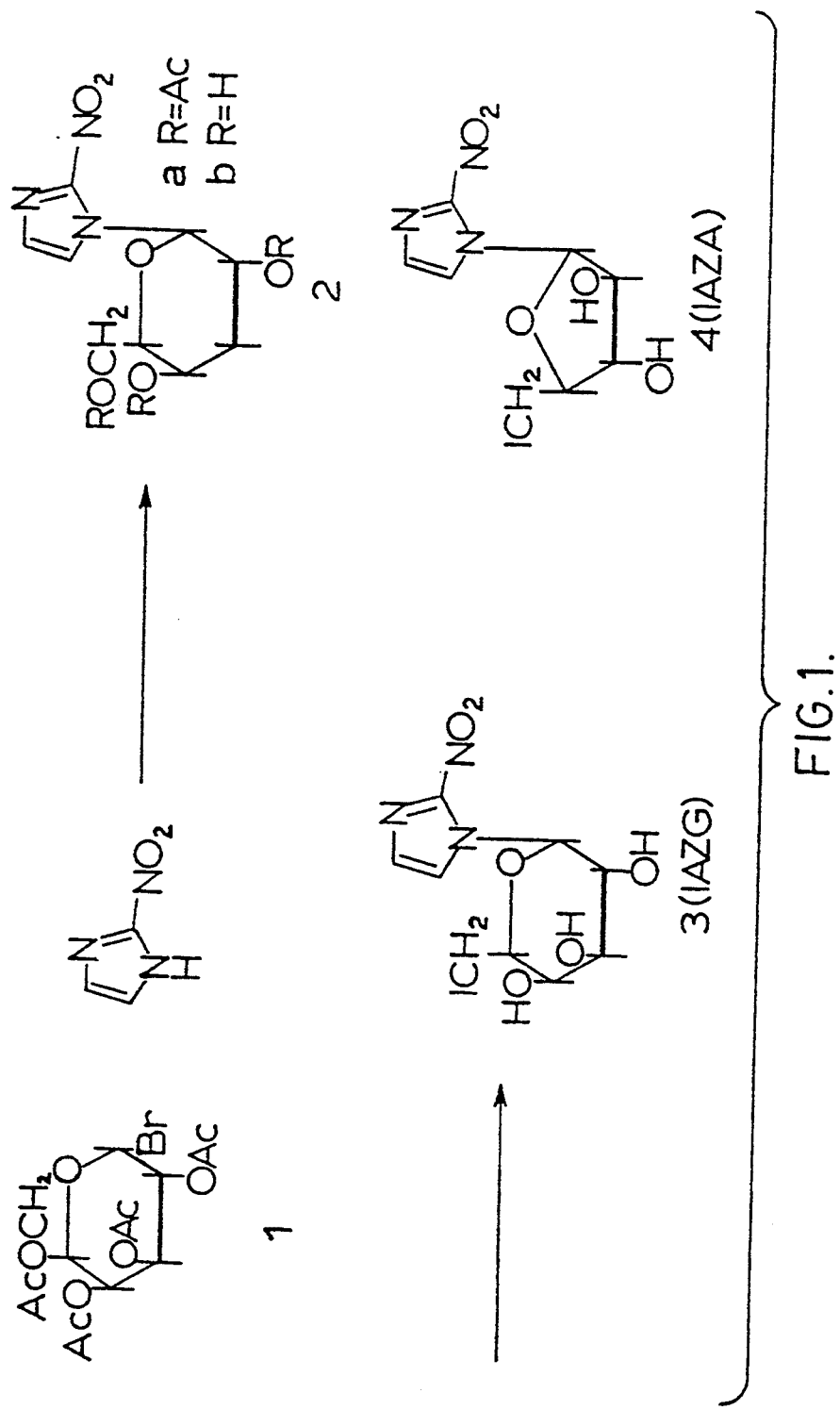
FIG. 1 is a scheme illustrating the synthesis of sugar coupled 2-nitroimidazoles IAZG and IAZA.

1-($\beta$-D-Galactopyranosyl)-2-nitroimidazole(2b in FIG. 1)

This compound was prepared by a modification of the procedure of Sakaguchi (17). 2-Nitroimidazole (220 mg, 1.9 mmol) was added to a stirred solution of tetra-O-acetyl-$\alpha$-bromogalactose (800 mg, 1.9 mmol) and mercuric cyanide (1.1 g, 4.4 mmol) in 100 ml of dry acetonitrile. After 12 hours at room temperature the solvent was removed and the residue taken up in dichloromethane and filtered. The filtrate was washed successively with saturated aqueous sodium carbonate, 30% aqueous potassium iodide and water. The organic layer was dried with anhydrous magnesium sulphate and evaporated to dryness. The residue was chromatographed on silica gel (60–200 mesh), using ethyl acetate:toluene (4:6) as eluant, to yield the tetra-O-acetyl intermediate (2a in FIG. 1) (631 mg, 73%). A portion of this product (500 mg, 1.12 mmol) was dissolved in 10 ml of 0.05M methanolic sodium methoxide. After 12 hours at room temperature the resultant virtually pure crystalline product (297 mg, 96% was isolated by vacuum filtration. MP, 220°–221° C.(dec). $^1$H NMR (DMSO-d$_6$) $\sigma$ 7.76 (1H, d, J=1.0 Hz, C$_5$—H); 7.20 (1H, d, J=1.0 Hz, C$_4$—H); 5.84 (1H, d, J=8.8 Hz, C$_{1'}$—H); 3.4–3.8 (6H, complex unresolved multiplet for sugar ring and C$_{6'}$—H). $^{13}$C NMR (DMSO-d$_6$) $\sigma$ 144.5 (C$_2$); 127.9 (C$_4$); 123.6 (C$_5$); 86.0 (C$_{1'}$); 78.8 (C$_{5'}$); 73.4 (C$_{3'}$); 70.7 (C$_{2'}$); 68.4 (C$_{4'}$); 60.4 (C$_{6'}$). MS (DIP E$_v$=70 eV) 275 (M+; 2%). Exact mass 275.0751, calc. 275.0753 for C$_9$H$_{13}$N$_3$O$_7$.

EXAMPLE 2

1-(6-iodo-6-deoxy-$\beta$-D-galactopyranosyl)-2-nitroimidazole (IAZG: 3 in FIG. 1):

A solution of the product of Example 1 (2b in FIG. 1) (300 mg, 1.09 mmol) in dry pyridine (15 mL) was treated with triphenylphosphine (572 mg, 2.18 mmol) and iodine (277 mg, 1.09 mmol of I$_2$) and the solution was stirred at 40° C. for 12 h. The reaction mixture was cooled, quenched with methanol (1 mL) and evaporated to dryness. The residue was applied to a silica gel column (60–200 mesh) and the required product eluted at 7% methanol in CHCl$_3$. The isolated and dried crystalline product (328 mg, 78%) was chromatographically pure. MP, 187°–188° C. (dec) . $^1$H NMR (CD$_3$OD) $\sigma$ 7.66 (1H, d, J=1.1 Hz, C$_5$—H); 7.08 (1H, d, J=−1.1 Hz, C$_4$—H); 6.02 (1H, d, J=9.0 Hz, C$_{1'}$—H); 4.06 (1H, d, J=3 Hz, C$_{4'}$—H); 3.92 (1H, dd, J$_{5'-6'}$=7.5 Hz, J$_{5'-6''}$=6.5 Hz, C$_{5'}$—H); 3.76 (1H, dd, J$_{2'-3'}$=9.5 Hz, J$_{2'-1'}$=9.0 Hz, C$_{2'}$—H); 3.60 (1H, dd, J$_{3'-2'}$=9.5 Hz, J$_{3'-4'}$=3 Hz, C$_{3'}$—H); 3.32 (1H, dd, J (gem)=10 Hz, J$_{6'-5'}$=6.5 Hz, C$_{6'}$—H); 3.23 (1H, dd, J (gem)-=10 Hz, J$_{6''-5'}$=7.5 Hz, C$_{6''}$—H). $^{13}$C NMR (CD$_3$OD) σ 144.0 (C$_2$); 128.5 (C$_4$); 123.7 (C$_5$); 86.9 (C$_{1'}$); 79.7 (C$_{5'}$); 74.9 (C$_{3'}$); 71.7 (C$_{2'}$); 70.4 (C$_{4'}$); 1.3 (C$_{6'}$). MS (DIP E$_v$=70 eV) 385 (M+;3%). Exact mass 384.9730. Calc. 384,9730 for C$_9$H$_{12}$N$_3$O$_6$I.

EXAMPLE 3

1-(2,3,5-Tri-O-benzoyl-β-D-arabinofuranosyl)-2-nitroimidazole

The coupling procedure of Sakaguchi (17) (12) was modified to give a higher yield and selective formation of the β-anomer. 2-Nitroimidazole (118 mg; 1.05 mmol) was added to a stirred solution of 1-bromo-2,3,5-tri-O-benzoyl-α-D-arabinofuranose (500 mg; 0.95 mmol) and mercuric cyanide (600 mg; 2.04 mmol) in dry acetonitrile (50 mL). The mixture was stirred for 6 hours at room temperature, after which the solvent was removed under vacuum. The residue was dissolved in dichloromethane (200 mL) and filtered. The filtrate was washed successively with saturated aqueous sodium hydrogen carbonate solution, 30% aqueous potassium iodide, and water, then dried over anhydrous magnesium sulfate. The solvent was evaporated under vacuum and the residue applied to a silica gel column and eluted with ethyl acetate:toluene=90:10 (v/v). The coupled product was recovered in 69% chemical yield (367 mg).

EXAMPLE 4

1-(β-D-Arabinofuranosyl)-2-nitroimidazole (AZA)

The product of Example 3 (250 mg; 0.45 mmol) was dissolved in methanolic ammonia (25 mL) and allowed to stand at 0° C. for 2 days. The solvent was removed under vacuum and the residue was washed 3 times with chloroform. The washed residue was dissolved in methanol and the title compound (AZA) was recrystallized from this solution in 92% (101 mg) recovered yield. MP. 192°-193° C. (lit. 160° C. (12)):

$^1$H NMR (CD$_3$OD) σ 7.65 (1H, d, J=1.3 Hz, C$_5$—H); (1H, d, J=1.3 Hz, C$_4$—H); 6.44 (1H, d, J (C$_{1'}$—C$_{2'}$)=1.3 Hz, C$_{1'}$—H); 4.50 (1H, m, C$_{4'}$—H); 4.25 (1H, m, C$_{2'}$—H); 4.14 (1H, m, C$_{3'}$—H); 3.78 (2H, m, C$_{5'}$—H). $^{13}$C NMR (CH$_3$OD) σ 145 (C$_2$); 128.1 (C$_4$); 125.2 (C$_5$); 97.1 (C$_{1'}$); 91.7 (C$_{4'}$); 84.0 (C$_{2'}$); 78.1 (C$_{3'}$); and 63.2 (C$_{5'}$). MS (DIP E$_v$=70 eν) 245 (M+; 5%). Exact mass 245.0467, calc. 245.0468 for C$_9$H$_{11}$N$_3$O$_6$.

EXAMPLE 5

1-(5-iodo-5-deoxy-β-D-arabino-furanosyl)-2-nitroimidazole (IAZA: 4 in FIG. 1)

AZA as prepared in Example 4 (100 mg; 0.4 mmol) in dry pyridine (5 mL) was mixed with triphenylphosphine (212 mg; 0.8 mmol) and iodine (101 mg; 0.40 mmol), and stirred for 4 hours at 30° C. The reaction was quenched with methanol (0.5 mL), after which the mixture was taken to dryness under vacuum. The residue was applied to a silica gel column. Triphenylphosphine oxide was washed from the column with CHCl$_3$, and compound 3 (IAZA) was subsequently eluted with CHCl$_3$:MeOH=95:5 (v/v). IAZA was recovered as a white crystalline solid (109 mg; 75% yield) by evaporation of the solvent. MP. 122° C. 1H NMR (CD$_3$OD) σ 7.52 (1H, d, J=0.9 Hz, C$_5$—H); 7.12 (1H, d, J=0.9 Hz, C$_4$—H); 6.52 (1H, s, C$_{1'}$—H); 4.63 (1H, dt, J$_{4',3'}$=1.7 Hz, J$_{4',5'}$=7.3 Hz, C$_{4'}$—H); 4.29 (1H, d, J$_{2',3'}$=1.6 Hz, C$_{2'}$—H); 4.26 (1H, dd, J$_{3',2'}$=1.6 Hz, J$_{3',4'}$=1.7 Hz, C$_{3'}$—H); 3.44 and 3.51 (2H, dd, J$_{5',5'}$=10.2 Hz, J$_{5',4'}$=7.3 Hz, C$_{5'}$≦H). $^{13}$C (CD$_3$OD) σ 144.8 (C$_2$); 127.7 (C$_4$); 124.3 (C$_5$); 96.4 (C$_{1'}$); 90.2 (C$_{4'}$); 83.1 (C$_{2'}$); 78.9 (C$_{3'}$); and 5.3 (C$_{5'}$). MS (DIP E$_v$=70 eV) 355 (M+; 3%). Exact mass 354.9624, calc. 354.9624 for C$_8$H$_{10}$N$_3$O$_5$I.

EXAMPLE 6

$^{125}$I-Labelled IAZG and IAZA were prepared by the following general procedure. Dry, no-carrier-added Na$^{125}$I in a 1 mL Reacti-Vial was treated with 1 or 2 mg of 3 or 4 in 20 μL of dry dimethyl formamide. After heating the sealed vial for 3.5 h at 70° C., the reaction mixture was chromatographed directly by HPLC and the radiolabelled products isolated. Purified, $^{125}$I-labelled IAZG and IAZA were stored as dry residues in multidose vials until required. Radiochemical yields of 80% and chemical and radiochemical purity in excess of 99% was typical with specific activity of about 7 GBq/mmol. Analogues radiolabelled with $^{131}$I and $^{123}$I have been prepared similarly.

EXAMPLE 7

Initial binding rates were measured (FIG. 8) at four concentrations of IAZA (3, 10, 30 and 100 μM), using normally oxygenated and hypoxic EMT-6 cell cultures as described previously (13). Similar studies at the same concentration of misonidazole were used as controls.

EXAMPLE 8 CELL UPTAKE STUDIES

Figure 5:
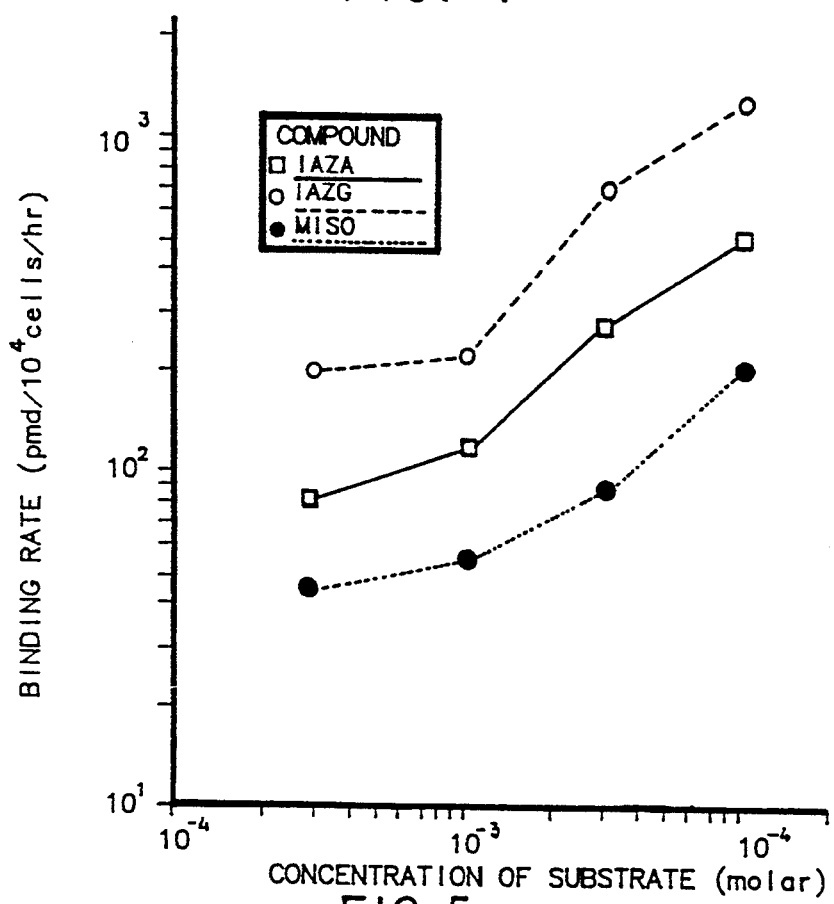
FIG. 5 shows initial binding rates of $^{125}I$-IAZG, $^{125}I$-IAZA and $^{14}C$-MISO to the acid insoluble fraction of EMT-6 cells under hypoxic conditions.

The uptake of test drugs into EMT-6 cell suspensions, under oxic and hypoxic conditions, was determined as described previously (18, 13). The data were analyzed in terms of drug binding to the macromolecular fraction at various times and at various test drug concentrations (FIG. 4). The initial binding rate, in units of pmol/10$^6$ cells per hour for each drug, was determined from the binding data (FIG. 5).

EXAMPLE 9 TOXICITY STUDIES

EMT-6 mouse fibrosarcoma cells in stirred cultures, as described previously (5), were exposed to various concentrations of the test drugs under hypoxic conditions. Cells were removed at various intervals and the colony-forming ability was assessed by plating the cells in drug-free complete MEM with 10% fetal calf serum. The data were used to construct plots of surviving fraction of EMT-6 cells against time of incubation with test drug at various drug concentrations (FIG. 2) as in Jette (13).

EXAMPLE 10 HYPOXIC CELL RADIOSENSITIZING ABILITY

The cytosidal effect of γ-radiation from a $^{137}$Cs irradiator, on EMT-6 mouse fibrosarcoma cells in culture, was determined by the colony-forming ability of aliquots removed from incubated irradiation vessels as described previously (13). Cell cultures were examined under oxic (air) and hypoxic incubation, with various concentrations of test drug, and at several doses of radiation. These data were used to construct post-irradiation survival curves (FIG. 3A and 3B).

EXAMPLE 11 TISSUE DISTRIBUTION AND EXCRETION

Tumor propagation of EMT-6 tumors in BALB/C mice was accomplished by subcutaneous injection of a cell suspension ($10^5$ cells in 0.1 mL) as described previously (10). Tumors reached about 10 mm in diameter ($\approx 0.5$ g) at 12 to 14 days, at which time each animal was given a bolus intravenous injection of $^{125}$I-labelled test drug via the tail vein (40 to 60 kBq in 0.1 mL). At set time periods the animals were asphyxiated with $CO_2$ and exsanguinated via cardiac puncture. Tissues were dissected, weighed wet into vials and counted for $^{125}$I-activity. Whole-body activity was determined by summation of total activity in tissues and in residual carcass, and blood activity was determined from the blood aliquot, assuming blood to be 6.5% of the total body weight.

EXAMPLE 12

Male BALB/c mice (20-25 g) were inoculated subcutaneously in the left flank with a suspension of murine EMT-6 cells ($10^5$ cells in 0.1 mL) (14). After 12 to 14 days, when the tumors reached the desired size (8-10 mm diameter), each mouse received a single intravenous (iv) injection of $^{125}$I-IAZA (59 kBq in 0.1 mL). Animals (6 per time interval) were exsanguinated by cardiac puncture immediately following asphyxiation in $CO_2$, at intervals of 15 min, 30 min, and 1, 2, 4, 8, 12 and 24 hr after injection of $^{125}$I-IAZA. Heart, lung, liver, spleen, muscle, bone, thyroid, kidney, stomach, small intestine, tail, tumor and skin were removed upon necropsy, weighed and analyzed for $^{125}$I using a Beckman Model 8000 gamma scintillation counter. The remaining carcass mass was also weighed and radioassayed.

Although certain preferred embodiments of the present invention have been described herein, the present invention is not limited to these embodiments but includes all compounds within the scope of the claims and their preparation and use in accordance with the claims.

1. Moulder, J. E. and Rockwell, S. (1984). Hypoxic fraction of solid tumors: Experimental techniques, methods of analysis and a survey of existing data. *Int. J. Radiat. Oncol. Biol. Phys.*, 10, 695-712.
2. Chapman, J. D., Franko, A. J. and Koch, C. J. (1983). The fraction of hypoxic clonogenci cells in tumor populations. In G. H. Fletcher, C. Nervi, and H. R. Withers, (Ed.), *Biological Bases and Clinical Implication of Tumor Radioresistance*, Masson, New York, pp. 61-73.
3. Dewey, D. L. (1960). Effect of oxygen and nitric oxide on the radiosensitivity of human cells in tissue culture. *Nature*, 186, 780-782.
4. Chapman, J. D. (1984). The detection and measurement of hypoxic cells in solid tumors. *Cancel*, 54, 2441-2449.
5. Chapman, J. D., Baer, K. and Lee, J. (1983). Characteristics of themetabolism indiced binding of misonidazole to hypoxic mannalian cells. *Cancel Res.*, 43, 1523-1528.
6. Garrecht, B. M. and Chapman, J. D. (1983). The labelling of EMT-6 tumors in BALB/C mice with $^{14}$C-misonidazole. *Brit. J. Radiol.*, 56, 745-753.
7. Biaglow, J. E., Varnes, M. E., Roizen-Towle, L., Clark, E. P., Epp, F. R., Astor, M. B. and Hall, E. J. (1986). Biochemistry of reduction of nitroheterocycles. *Biochem. Pharmacol.*, 35, 77-90.
8. Jette, D. C., Wiebe, L. I. and Chapman, J. D. (1983). Synthesis and in vivo studies of the radiosensitizer 4-($^{12}$Br)bromomisonidazole, *Int. J. Nucl. Med. Biol.*, 10, 205-210.
9. Rasey, J. S., Krohn, K. S. and Freauff, S. (1982). Bromomisonidazole: Synthesis and characterization of a new radiosensitizer, *Radiat. Rse.*, 91, 542-554.
10. Wiebe, L. I., Jette, D. C. and Chapman, J. D. (1984). Electron affinic compounds for labelling hypoxic cells. The synthesis and characterization of 1-(2-(2-iodophenoxy)ethyl)-2-nitroimidazole. *Nucelarmedizine*, 23, 63-67.
11. Mercer, J. R., Wiebe, L. I. and Chapman, J. D. (1988). Synthesis of eradiolabelled 2-nitroimidazoles for non-invasive estimation of hypoxic tumors. *J. Lab. Comp. Radiopharm.*, 25, 107-108.
12. Jerabek, P. A., Patrick, T. B., Kilbourn, M. R., Dischino, D. D. and Welch, M. J. (1986). Synthesis and biodistribution of $^{18}$F-labeled fluoro misonidazoles: potential in vivo markers of hypoxic tissue. *Appl. Radiat. Isot.*, 37, 599-605.
13. Jette, D. C., Wiebe, L. I., Flanagan, R. J., Lee, J. and Chapman, J. D. (1986). Iodoazomycin riboside, (1-5'-iodo-5'deoxyribofuranosyl)-2-nitroimidazole), a hypoxic cell marker. *Radiat. Res.*, 105, 169-179.
14. Wiebe, L. I., Jette, D. C., Chapman, J. D., Flanagan, R. J. and Meeker, B. E. (1986). Iodoazomycin riboside (1-5'-iodo-5'deoxyribofuranosyl)-2-nitroimidazole), a hypoxic cell marker. In vivo evaluation in experimental tumors. In Nuclear Medicine in Clinical Oncology. Heidelberg, Springer-Verlag, pp. 402-407.
15. Phillips, T. L., Wasserman, T. H., Stetz, J. and Brady, L. W. (1982). Clinical trials of hypoxic cell sensitzers. *Inc. J. Radiat. Oncol. Biol. Phys.*, 8, 327-334.
16. Rockwell, S. and Kallman, R. F. (1973). Cellular sensitivity and tumor radiation response in the EMT-6 tumor cell system. *Radiat. Res.*, 53, 281-294.
17. Sakaguchi, M., Laroquette, C. A., Agrawal, K. C.: Potential radiosensitizing agents. 6. 2-Nitroimidazole nucleosides:Arabinofuranosyl and hexopyranosyl analogs. *J. Med Chem* 1983, v.26, p. 20-24.
18. Chapman, J. D., Blakeley, E. A., Smith, K. C. and Urtasun, R. C. (1977). Radiobiological characterization of the inacrtiviting events produced in mammalian cells by helium and heavy ions. *Int. J. Radiat. Oncol. Biol. Phys.*, 3, 97-102.

The embodiments of the invention in which an exclusive property or privilege is claimed are defined as follows:

1. A method for the diagnostic imaging of hypoxic tissue in a mammal comprising the steps of
   (a) administering to the mammal a nucleoside having the formula

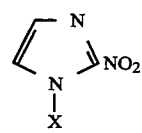

wherein X is arabinofuranose monosaccharide, said monosaccharide having a hydrogen or hydroxide substituent replaced by a γ-emitting halogen, wherein said nucleoside is taken up selectively by the hypoxic tissue; and (b) determining the γ-emission from said halogen.

2. A method according to claim 1 wherein said mammal is a human.

3. A method according to claim 1 wherein said nucleoside is 1(5-deoxy-5-iodo-β-D-arabinofuranosyl)-2-nitroimidazole, and wherein said 5-iodo substituent is selected from the group consisting of $^{125}$I, $^{124}$I, $^{123}$I and $^{131}$I.

4. A method in accordance to claim 1 wherein the hypoxic tissue is located in a tumor.

5. A method in accordance with claim 1 wherein the hypoxic tissue is ischaemic heart tissue.

* * * * *

UNITED STATES PATENT AND TRADEMARK OFFICE
CERTIFICATE OF CORRECTION

PATENT NO. : 5,401,490

DATED : March 28, 1995

INVENTOR(S) : Wiebe et al

It is certified that error appears in the above-identified patent and that said Letters Patent is hereby corrected as shown below:

ON THE COVER PAGE:

Inventor, "Vijayalakashmi" should be -- Vijayalakshmi --.

References, publications, column 2, line 1, "-5-" should be -- 5'--; line 2, omit "-'"; line 4, "C" should be -- C. --.

Column 1, line 34, "one" should be -- One --.

Column 2, line 62, before "According" begin a new paragraph.

Column 8, line 24, after "1)" insert a --:--. and do not indent.

Column 9, line 6, "$C_{3'-H)}$" should be -- $C_{3'}$-H) --.

Column 10, line 1, "1H" should be -- $^1$H --.

Column 10, line 5, "2°" should be -- 2' --.

Column 10, line 7, "$\leq$" should be -- - --.

Column 10-11, in the headings, Examples 8-11, insert a space after the numerals 8, 9, 10 and 11.

UNITED STATES PATENT AND TRADEMARK OFFICE
CERTIFICATE OF CORRECTION

PATENT NO. : 5,401,490
DATED : March 28, 1995
INVENTOR(S) : Wiebe et al

It is certified that error appears in the above-indentified patent and that said Letters Patent is hereby corrected as shown below:

Column 10, line 68, "FIG." should be --FIGS.--.

Signed and Sealed this

Fourth Day of July, 1995

BRUCE LEHMAN

Attest:

Attesting Officer

Commissioner of Patents and Trademarks